United States Patent [19]

Magolda et al.

[11] Patent Number: 4,702,864

[45] Date of Patent: Oct. 27, 1987

[54] ANALOGS OF PLATELET ACTIVATING FACTOR

[75] Inventors: Ronald L. Magolda, Aston, Pa.; Pasquale N. Confalone, Wilmington; Paul R. Johnson, Newark, both of Del.

[73] Assignee: E. I. Du Pont de Nemours and Company, Wilmington, Del.

[21] Appl. No.: 884,669

[22] Filed: Jul. 16, 1986

Related U.S. Application Data

[63] Continuation of Ser. No. 780,770, Sep. 27, 1985.

[51] Int. Cl.[4] .......................... C08H 3/00; C08H 9/02
[52] U.S. Cl. ................................. 260/402.5; 260/397; 260/403; 558/170
[58] Field of Search ..................... 260/399, 402.5, 403; 558/170

[56] References Cited

FOREIGN PATENT DOCUMENTS 3307924 9/1984 Fed. Rep. of Germany ...... 260/925
2020663 11/1979 United Kingdom ................ 260/403

OTHER PUBLICATIONS

Garrigues et al, CA102:131799(q), (1987).
Garrigues et al, *Synthesis*, (1984), (10), pp. 870–872.

*Primary Examiner*—Charles F. Warren
*Assistant Examiner*—Elizabeth A. Hanley

[57] ABSTRACT

1-Thioether-1-acylaminophosphatidylcholine compounds are structural analogs of platelet activating factor and useful for inhibition of phospholipase $A_2$, reduction of blood pressure, and alleviation of inflammation.

26 Claims, No Drawings

ANALOGS OF PLATELET ACTIVATING FACTOR

This application is a continuation of application Ser. No. 780,770 filed 09/27/85.

BACKGROUND OF THE INVENTION

The present invention relates generally to phosphatidyl choline compounds useful as pharmaceuticals which are analogs of 1-O-alkyl-2-acetyl-sn-glyceryl-3-phosphorylcholine, also known as platelet activating factor or PAF-acether.

Platelet activating factor (PAF-acether) is a potent mediator of anaphylaxis and inflammation. Among its physiological effects are activation of blood platelets and neutrophils and antihypertensive activity related to effects on smooth muscle cells.

Phospholipase $A_2$ is a phospholipid-hydrolyzing enzyme which is involved in the physiological response to PAF-acether. Inhibitors of this enzyme are useful in regulating various aspects of phospholipid biochemistry in vivo.

Tence et al., *Biochimie* 63: 723 (1981), disclose fourteen structural analogs of PAF-acether which are tested for platelet aggregating activity. Although several of the compounds tested were active, none contained a sulfur at the C-1 position nor a nitrogen at the C-2 position of the glycerol. This reference suggests that an ether linkage at position C-1 of the sn-glycerol and a short acyl chain at position C-2 are required for activity.

Hadvary et al., *Thrombosis Research* 30: 143 (1983), disclose structures of 26 synthetic analogs of PAF-acether and the relative activities of the disclosed compounds in triggering aggregation of rabbit and human platelets. All analogs disclosed were characterized by an ether-alkyl linkage at the C-1 position. Of the compounds tested, only those having short chain ester moieties at the C-2 position were active. Replacement at the C-2 position by formyl as well as by the butyryl esters significantly degraded activity.

Chandrakumar et al., *Tetrahedron Letters* 22: 2949 (1981), disclose use of serine in a synthetic method for making analogs of PAF-acether. The disclosed method yielded compounds of desired chirality for possible use as phospholipase inhibitors. Synthesis of 1-O-acetoalkyl-2-palmitoylamido-2-deoxy-3-O-phosphorylcholine is disclosed. No results of biological testing are provided.

Betzing et al., European Published Patent Application No. 43,472 (1981), disclose analogs of PAF-acether having a thioether linkage at position C-1 of the glycerolphosphorylcholine nucleus. These compounds exhibited anti-hypertensive activity.

SUMMARY OF THE INVENTION

The present invention provides compounds of the formula

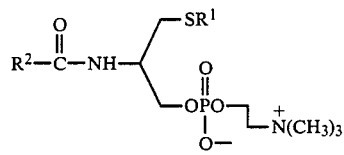

and physiologically acceptable salts thereof, wherein $R^1$ is $C_1-C_{25}$ alkyl, $C_1-C_{25}$ alkenyl, $C_6-C_{30}$ aryl, or $C_7-C_{30}$ aralkyl or alkaryl; and $R^2$ is hydrogen, $C_1-C_{25}$ alkyl, $C_6-C_{30}$ aryl, $C_7-C_{30}$ aralkyl or alkaryl, $C_1-C_{25}$ alkoxy, $C_1-C_{25}$ alkenyloxy, $C_6-C_{30}$ aryloxy, or $C_7-C_{30}$ aralkyloxy or alkaryloxy.

The present invention also provides therapeutic compositions comprising the foregoing compounds, and methods for using the compositions to inhibit phospholipase $A_2$ activity, alleviate hypertension, and alleviate inflammation in warm-blooded animals.

The present invention also provides a process for preparing the compounds of the invention, comprising
(a) protecting an acid salt of
(L)-methylserate by reaction with an ethyl benzimidate salt in the presence of base to yield a
(D)-2-phenyl-4-carbomethoxy-4,5-dihydro-oxazole ester 3 of formula

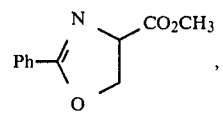

(b) reducing the ester 3 by treatment with lithium aluminum hydride to provide an alcohol 4 of formula

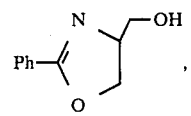

(c) reacting the alcohol 4 with a methanesulfonyl compound to provide a chiral mesylate compound 5 of formula

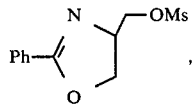

(d) displacing the mesylate group of compound 5 with a sodium alkylthiolate, optionally via a thioacetate intermediate, to provide a thioether 7 of formula

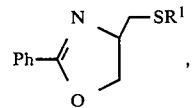

(e) reacting the thioether 7 with acetic anhydride to provide a 2-acetamido-3-benzoate, and cleaving the benzoate by base hydrolysis to yield a 3-substituted-thioester-2-acetamido-glycerol 8 of formula

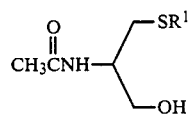

(f) phosphorylating the glycerol 8 to provide a cyclic triester phosphate 9 of formula

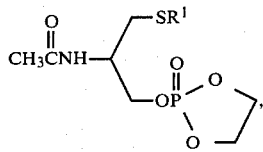

(g) reacting the cyclic triester phosphate 9 with trimethylamine to provide a compound 10 of formula I;
or, in the alternative,
(e') reacting the thioether 7 with sulfuric acid to provide an amino alcohol 11 of formula

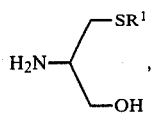

(f') acylating the alcohol 11 with an $R^2$-substituted acylating agent and subjecting the resulting acyl intermediate to base hydrolysis to provide an amino-glycerol 12 of formula

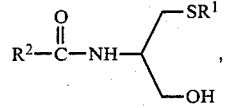

(g') phosphorylating the amino-glycerol 12 to provide a cyclic triester phosphate 9a of formula

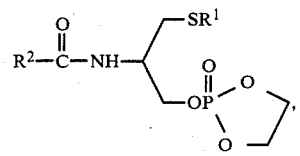

(h') reacting the cyclic triester phosphate 9a with trimethylamine to provide a compound 10 of formula I; wherein $R^1$ and $R^2$ are defined as in claim 1.

The present invention also provides a critical intermediate of the foregoing process, compound 7, having the formula

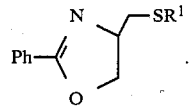

DETAILED DESCRIPTION OF THE INVENTION

The phosphatidyl choline analogs of formula I above are characterized by a thioether linkage to an alkyl, alkenyl, aryl, aralkyl, or alkaryl moiety at position C-1 of the glycerolphosphorylcholine nucleus, and by an amide linkage at position C-2. The amide bridge can link hydrogen or alkyl, aryl, aralkyl, alkaryl, alkoxy, alkenyloxy, aryloxy, alkaryloxy, or alkaryloxy groups to the glycerolphosphorylcholine nucleus.

As used throughout the specification, either individually or as part of a larger group, "alkyl" means a linear, saturated aliphatic radical. "Alkenyl" means a linear, unsaturated aliphatic radical having one or more carbon-carbon double bonds. "Aryl" means an aromatic radical, e.g., phenyl. "Aralkyl" means a linear aliphatic radical comprising an aryl group or groups. "Alkaryl" means a aryl radical having one or more linear aliphatic substituents. "Alkoxy" means an alkyl radical joined by an oxygen atom to the glycerolphosphorylcholine nucleus. Similarly, "alkenyloxy," "aryloxy," "alkaryloxy," and "alkaryloxy" mean alkenyl, aryl, alkaryl, and alkaryl radicals having an oxygen atom at the point of substitution on the parent molecule.

Preferred compounds within the scope of the present invention are those compounds of formula I wheren $R^1$ is $C_{14}-C_{18}$ alkyl or $C_{14}-C_{18}$ alkenyl, and $R^2$ is $C_1-C_{25}$ alkyl, $C_1-C_{25}$ alkoxy, or phenyl. Especially preferred are those compounds wherein $R^1$ is a 9Δ-$C_{18}H_{35}$ alkenyl group and $R^2$ is methyl or phenyl; $R^1$ is a $C_{18}H_{37}$ alkyl group and $R^2$ is methyl, methoxy or a $C_{17}H_{35}$ alkyl group; and $R^1$ is a $C_{16}H_{33}$ alkyl group and $R^2$ is methyl, methoxy, phenyl, or a $C_{17}H_{35}$ alkyl group.

SUMMARY OF SYNTHETIC PROCEDURES

Processes for preparing compounds of formula I are illustrated and summarized below:

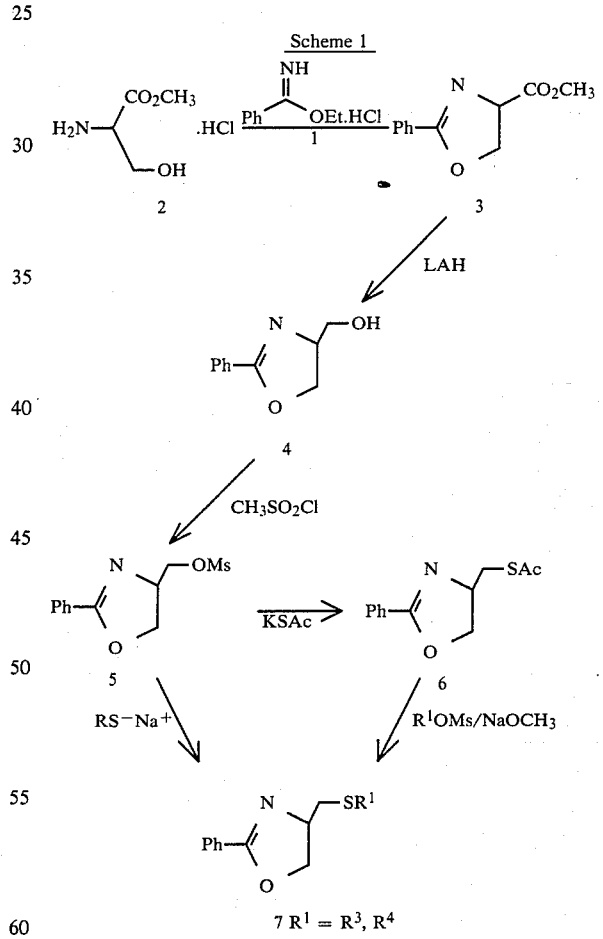

The objective of the first series of reactions in the general synthetic scheme is synthesis of intermediates allowing substitution of various alkyl-, alkenyl-, and aryl-thioethers at position $R^1$ of the final chiral phospholipid compounds of formula I. This series of reactions is illustrated in Scheme 1, above, using (L)-methylserate hydrochloride 2 as starting material. The amino alcohol of 2 is first protected by reaction with ethyl benzimidate hydrochloride 1 in the presence of base (triethylamine), providing (D)-2-phenyl-4-carbomethoxy-4,5-dihydro-oxazole 3.

To introduce the upper side chains, two routes were devised so that both saturated ($R^3$) and unsaturated ($R^4$) alkyl chains could be accommodated. To prepare saturated thioethers, ester 3 is reduced with lithium aluminum hydride in diethyl ether to provide alcohol 4. Alcohol 4 is then mesylated with methanesulfonyl chloride to give the versatile chiral mesylate compound 5. The mesylate group of compound 5 is directly displaced with saturated sodium alkylthiolates by adding the alkyl mercaptans and the mesylates 5 to freshly prepared sodium methoxide in methanol, converting compound 5 into thioether 7. To prepare derivatives of compound 7 having unsaturated thioether substituents at position $R^1$, preparation of thioacetate 6 is necessary. Compound 6 is obtained by incubating mesylate 5 with potassium thioacetate in acetonitrile and dimethylsulfoxide. The acetate is hydrolyzed by adding freshly generated sodium methoxide in methanol. The addition of unsaturated alkyl mesylates to the reaction mixture provides thioether 7.

With synthetic routes to a variety of alkyl-, alkenyl-, aryl-thioethers complete, amino substitution is addressed as illustrated in Scheme 2, below. In this series of reactions, the protection of phenyl-4,5-dihydro-oxazole is removed and substitution is performed simultaneously.

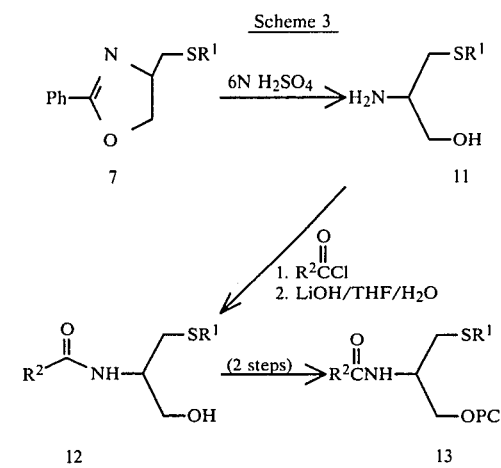

As indicated in Scheme 3, the protection of phenyl-4,5-dihydro-oxazole 7 is removed with sulfuric acid to give amino alcohol 11. Acylation of amino alcohol 11 with a variety of acylating agents ($ClCO_2CH_3$, $ClCOR^2$, $HCO_2COCH_3$; $R^2$=alkyl, alkenyl, aryl) followed by selective base hydrolysis (LiOH) provides the corresponding substituted amino-glycerols 12. Elaboration to the phospholipids 13 proceeds in the same manner described for converting 8 to 10 in Scheme 2.

SYNTHETIC EXAMPLES

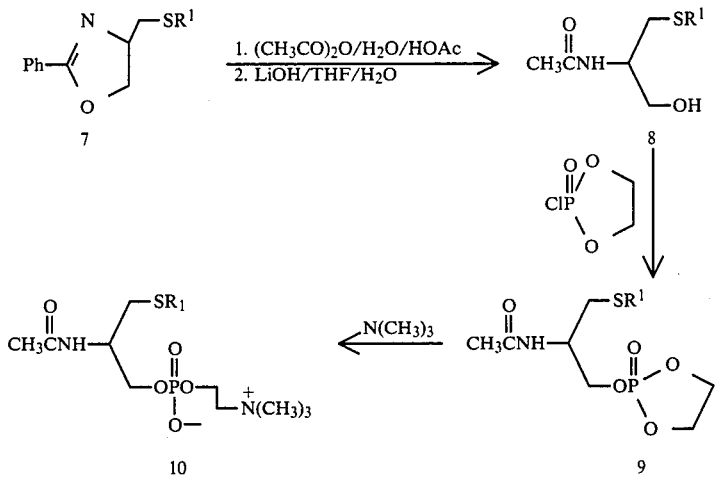

This is accomplished by adding acetic anhydride to an aqueous acetic acid solution of 7 and refluxing for about 2 hours to generate product 2-acetamido-3-benzoate. Cleavage of the benzoate by base hydrolysis (LiOH) provides the requisite 3-(alkyl, alkenyl, aryl)-thioester-2-acetamido-glycerol 8 in good yield.

The (alkyl, alkenyl, aryl)-thioester-2-acetamido-glycerol 8 is phosphorylated in tetrahydrofuran with 2-chloro-2-oxo-1,2,3-dioxaphospholane in the presence of triethylamine. The resulting cyclic triester phosphate 9 is then exposed to excess trimethylamine for 48 hours at about 65° C., yielding the desired acetamido phospho-lipid 10.

Alternative procedures for amino substitutions are shown in Scheme 3, below.

The following examples describe synthetic procedures employed in production of particular compounds within the scope of formula I. Unless otherwise indicated, all parts and percentages are by weight and all temperatures are reported in degrees Celsius (°C.).

The following abbreviations are employed in the examples:
NMR: Nuclear magnetic resonance spectroscopy
IR: Infrared spectroscopy
HRMS: High resolution mass spectrometry
FAB-MS: Fast atom bombardment, mass spectrometry
EA: Elemental analysis Particular intermediates or products are identified by reference to the numbered compounds in the general synthetic procedures summarized above. Physical data for various compounds produced by procedures substantially corresponding to the description contained in each example are provided following individual examples. The following key identifies particular compounds:

$$R^2-\overset{O}{\underset{\|}{C}}-NH-\underset{\underset{O^-}{\overset{O}{\underset{\|}{-OPO-}}}}{\overset{-SR^1}{\underset{}{}}}\phantom{-}\overset{+}{N(CH_3)_3}$$

| First Suffix | $R^1$ | Second Suffix | $R^2$ |
|---|---|---|---|
| A | $9\Delta\text{-}C_{18}H_{35}$ | none | $CH_3$ |
| B | $C_{18}H_{37}$ | I | $C_{17}H_{35}$ |
| C | $C_{16}H_{33}$ | II | $CH_3O$ |
| D | $C_8H_{17}$ | III | H |
| E | $C_6H_{13}$ | IV | Ph |

EXAMPLE 1

Synthesis of Compounds of Formula I

A. Preparation of Ethyl benzimidate hydrochloride (1)

Dry (distilled from sodium) ethanol (9 g) was added to freshly distilled benzonitrile (10 g). The resulting mixture was cooled to 0° and then saturated with anhydrous hydrogen chloride gas. This mixture was then allowed to stand for 18 hours, during which time tan colored crystals formed. These crystals were taken up in ether and washed several times with 2N NaOH, followed by aqueous extraction to give an oil. This oil was dissolved in dry (over sodium and benzophenone) ether (20 mL), cooled to 0°, and then exposed to anhydrous hydrogen chloride. After 2 hours, white crystals were obtained (9.4 g, 55% yield) with a melting point consistent with ethyl benzimidate hydrochloride (1) (J. Org. Chem. 30:699 (1965)).

B. Preparation of (D)-2-phenyl-4-carbomethoxy-4,5-dihydro-oxazole (3)

Ethyl benzimidate hydrochloride (1) (4.73 g) was dissolved in dry (distilled over calcium hydride) dichloromethane (250 mL). 1-Methylserate hydrochloride (2) (4.33 g) was introduced to this solution followed by dropwise addition of triethylamine (7.8 mL) which had been dissolved in dichloromethane (10 mL). The resulting reaction mixture was stirred for about 24 hours at about 23° and then concentrated in vacuo. The residue was dissolved in water (100 mL) and then extracted with ether (4×100 mL). The resulting organic extracts were combined, washed with saturated sodium chloride, and then dried over magnesium sulfate. Filtration and concentration in vacuo supplied only the desired product (D)-2-phenyl-4-carbomethoxy-4,5-dihydro-oxazole (3) (5.0 g, 87% yield).

(3): $[\alpha]^{25} = +142.5° \pm 0.8°$ (c=1.02, cyclohexane); +125.1°±0.8° (c=1.17, ethanol), +113.8°±0.8° (c=1.06, methanol); NMR (300 MHz CDCl$_3$): 8.00 (d, j=6 Hz, 2H, phenyl), 7.23 (m, 3H, phenyl), 5.00 (dd, j=7.0 Hz, 5.0 Hz, 1H, CHN), 4.70 (m, 2H, CH2$_O$), 3.80 (s, 3H, OCH$_3$); IR (CHCl$_3$): 2920 (s) 2850 (s), 1740 (s), 1640 (s, C=N), 1370 (s), 130 (m), 1050 (s), 900 (m).

C. Preparation of (D)-2-phenyl-4-hydroxymethyl-4,5-dihydro-oxazole (4)

Crude (D)-2-phenyl-4-carbomethoxy-4,5-dihydrooxazole (5.0 g) (3) was dissolved in dry (distilled over sodium and benzophenone) diethyl ether (200 mL). This solution was cooled to 0° and kept under a nitrogen atmosphere while lithium aluminum hydride (0.44 g) was slowly added over a period of about 30 minutes. The resulting reaction mixture was then permitted to warm to about 23°, and then stirred for an additional 4 hours. Complete conversion had occurred as shown later by thin layer chromatography (TLC) analysis. The reaction mixture was then recooled to 0°, quenched by addition of sodium sulfate decahydrate (5.0 g), stirred for 1 hour, filtered and concentrated in vacuo to provide the desired (D)-2-phenyl-4-hydroxymethyl-4,5-dihydro-oxazole (4) (3.5 g, 81% yield).

(4): $[\alpha]^{25} = +53.4° \pm 0.8°$ (c=1.03, methanol); NMR (90 MHz, CDCl$_3$): 8.00 (m, 2H, phenyl), 7.35 (m, 3H, phenyl), 4.65 (s, 1H, OH), 4.50 (m, 3H, CH2O, CHN), 3.80 (m, 2H, CH2O); IR (neat): 3400 (bs, OH), 2900 (s), 1645 (s, C=N), 1360 (s), 1060 (s), 700 (s).

D. Preparation of mesylate (5)

Methanesulfonyl chloride (1.25 mL) and triethylamine (3.1 mL) was added, under nitrogen, to a dichloromethane solution containing (D)-2-phenyl-4-hydroxymethyl-4,5-dihydro-oxazole (2.6 g) (4) which had been cooled to 0°. After two hours, when the reaction was complete as shown by thin layer chromatography of a sample (r$_f$=0; 5% acetone in CH2Cl2), it was quenched by addition of water (100 mL). Isolation of (5) was achieved by extracting the aqueous phase with dichloromethane (3×100 mL) and then washing the combined organic fractions successively with saturated sodium bicarbonate solution, water, and saturated sodium chloride solution. The resulting organic fraction was dried (magnesium sulfate) and concentrated in vacuo to provide the crude mesylate (5) (3.74 g, 100% yield) which was routinely used directly in the next step.

5: NMR (360 mHz, CDCl$_3$): 7.95 (m, 2H, phenyl), 7.45 (m, 3H, phenyl), 4.62 (m, 1H, CHN), 4.55 (m, 1H, CH2O), 4.40 (m, 3H, CH2O), 3.05 (s, 3H, CH$_3$); IR (CHCl$_3$): 2980 (m), 2960 (m), 2900 (m), 1645 (s), 1570 (m), 1450 (m), 1360 (s), 1170 (s), 1060 (m), 970 (s).

E. Synthesis of thioacetate (6)

Crude mesylate (2.55 g) (5) was dissolved in dry (distilled over calcium hydride) dimethylsulfoxide (50 mL) and maintained under an argon atmosphere. Potassium thioacetate (5.7 g) was introduced to this reaction mixture at about 23° and then the reaction mixture was heated and maintained at 45° for three hours. At this time the reaction was complete as shown by thin layer chromatography (5% methanol in chloroform). After cooling to about 23°, the reaction mixture was diluted with diethyl ether (200 mL) and quenched with water (100 mL). The resulting organic layer was successively washed with water (3×50 mL), saturated sodium bicarbonate solution (2×50 mL); and saturated sodium chloride solution (50 mL), then dried over magnesium sulfate, filtered, and concentrated in vacuo. The resulting residue was purified by silica gel chromatography (5% methanol in chloroform) to provide pure thioacetate (6) (2.03 g, 86% yield).

6: NMR (90 MHz, CDCl$_3$), 7.90 (m, 2H, phenyl), 7.40 (m, 3H, phenyl), 4.50 (m, 2H), 4.05 (m, 1H, CHN), 3.20 (d, j=6 Hz, 2H, CH2S), 2.35 (s, 3H, CH$_3$CO); IR (CHCl$_3$): 2910 (s), 1695 (s, COS), 1645 (s, C=N), 1380 (s), 1140 (s), 1055 (s).

E. Preparation of (D)-2-phenyl-4-octadec-9-enylthiomethyl)-4,5-dihydro-oxazole (7A)

Freshly cut sodium (0.7 g) was added to anhydrous methanol (50 mL) at 0° under a nitrogen atmosphere. When the sodium was completely dissolved (about 2 hours), a methanol solution (200 mL) containing thioacetate (5.0 g) was added and the mixture was stirred for 0.5 hours at 0°. Oleic mesylate (10.0 g) was added to the reaction mixture, which was then slowly warmed (1 hour) to 70° and maintained at 70° for 24 hours. The reaction mixture was then cooled to about 23° and diluted with dichloromethane. After three extractions with dichloromethane, the organic fractions were combined and washed with saturated sodium chloride solution, dried over magnesium sulfate, filtered, and then concentrated in vacuo to give a crude residue. Silica gel chromatography ($R_f$=0.45, 15% ethyl acetate in hexane) provided 8.1 g (86% yield) of the desired compound 7A, (D)-2-phenyl-4-(octadec-9-enyl-thiomethyl)-4,5-dihydro-oxazole.

7A: NMR (360 MHZ, CDCl$_3$): 7.95 (m, 2H, phenyl), 7.33 (m, 1H, phenyl), 7.25 (m, 2H, phenyl), 5.38 (m, 2H, olefin), 3.83 (m, 1H, CH2O), 3.63 (m, 1H, CH2O), 3.23 (m, 1H, NCH), 2.60 (d, j=8 Hz, 2H, CH2S), 2.35 (t, j=7.0 Hz, 2H, CH2S), 1.95 (m, 4 h), 1.5–1.15 (m, 24H), 0.87 (t, j=7.0 Hz, 3H, CH$_3$); IR (CHCl$_3$): 3000 (s), 2910 (s), 2850 (s), 1645 (s, C=N), 1420 (s), 1230 (s), 1190 (s), 1040 (m), 925 (m).

F. Preparation of (D)-2-phenyl-4-(octadecylthiomethyl)-4,5-dihydro-oxazole (7B)

Freshly cut sodium metal (0.28 g) was added slowly to anhydrous methanol (35 mL) at 0° under a nitrogen atmosphere. After the sodium was completely dissolved (0.5 hour at 0° C. then 1 hour at room temperature), the reaction mixture was recooled to 0° C. and octadecylmercaptan (2.86 g) and (D)-2-phenyl-4-(methanesulfonyl hydroxymethyl)-4,5-dihydro-oxazole (5) (2.40 g) were added sequentially. The reaction temperature allowed to warm to about 23° over a period of about 1 hour, and then increased to 75° and maintained at 75° for 6 hours. The reaction was then complete, as determined by thin layer chromatography ($R_f$ (7B)=0.45, 15% ethylacetate in hexane). The reaction was diluted with dichloromethane (100 mL) and quenched with water (50 mL). Extraction of the combined dichloromethane extracts (2×50 mL) with saturated sodium chloride solution, followed by drying over magnesium sulfate, filtration, and concentration in vacuo afforded crude 7B. Silica gel chromatography provided the pure (D)-2-phenyl-4-(octadecylthiomethyl)-4,5-dihydro-oxazole (7B) in a good yield (2.8 g, 67% yield).

7B: m.p.=78°–79°, $[\alpha]^{25}$=−2.3±2.0 (C=0.98, cyclohexane); NMR (360 MHz, CDCl$_3$): 7.95 (m, 2H, phenyl), 7.40 (m, 3H, phenyl), 4.50 (m, 2H, CH2O), 4.30 (m, 1H, CHN), 3.00 (dd, J=13 Hz, 3 Hz, 2H, CH2S), 2.60 (t, J=6 Hz, 2H, CH2S), 1.60 (m, 2H, CH2CH2S), 1.30–1.20 (m, 30H), 0.88 (s, 3H, CH$_3$); IR (CHCl$_3$): 3000 (s), 2920 (s), 2850 (s), 1645 (s, C=N), 1420 (s), 1230 (s), 1190 (s), 1040 (m), 925 (m).

7C: (71% yield); NMR (300 MHz, CDCl$_3$), 7.90 (m, 2H, phenyl), 7.40 (m, 3H, phenyl), 4.50 m, 2H, CH2O), 4.25 (m, 1H, CHN), 3.00 (dd, J=13 Hz, 3 Hz, 2H, CH2S), 2.60 (t, J=7.0 Hz, 2H, CH2S), 1.60 (m, 2H, CH2CH2S), 1.40–1.20 (m, 26H), 0.90 (t, J=7.0 Hz, 3H, CH$_3$); IR (CHCl$_3$): 3005 (s), 3000 (s), 2910 (s), 2850 (s), 1645 (s, C=N), 1420 (s), 1230 (s), 1190 (s), 1040 (m), 925 (m).

7D: (55% yield); NMR (360 MHz, CDCl$_3$): 7.95 (m, 2H, phenyl), 7.40 (m, 3H, phenyl), 4.50 (m, 2H) CH2O), 4.30 (m, 1H, CHN), 3.00 (dd, J=14 Hz, 2 Hz, 2H, CH2S), 2.60 (t, J=7.0 Hz, 2H, CH2S), 1.60 (m, 2H, CH2CH2S), 1.40–1.20 (m, 10H), 0.90 (t, J=7.0 Hz, 3H, CH$_3$); IR (CHCl$_3$): 2910 (s), 2850 (m), 1645 (s, C=N), 1450 (m), 1360 (m), 1060 (m), 980 (m).

7E: (50% yield), NMR (360 MHz, CDCl$_3$): 7.95 (m, 2H, phenyl), 7.40 (m, 3H, phenyl), 4.50 (m, 2H, CH2O), 4.30 (m, 1H, CHN), 3.00 (dd, J=4.0 Hz, 14.0 Hz, 2H, CH2S), 2.60 (t, J=7.5 Hz), 2H, CH2S), 1.60 (m, 2H, CH2CH2S), 1.40–1.20 (m, 6H), 0.90 (t, J=7.0, 3H, CH$_3$); IR (CHCl$_3$): 2980 (s), 2920 (s), 2850 (m), 1645 (s), 1470 (m), 1360 (s), 1300 (m), 1260 (m), 1080 (m), 1060 (m), 1030 (m), 960 (m).

F. Preparation of (D)-2-acetamido-3-octadecylthioglycerol (8B)

Freshly distilled acetic anhydride (20 mL) and water (5 mL) were added to a glacial acetic acid (40 mL) solution of (D)-2-phenyl-4-(octadecylthiomethyl)-4,5-dihydro-oxazole (7B) (0.54 g) at about 23°. The reaction mixture was stirred overnight (about 18 hours) at about 23°, but very little product formed as observed by thin layer chromatography. The reaction mixture was then refluxed for 3 hours at 100°, which resulted in the complete (as determined by thin layer chromatography) consumption of the starting material 7B. The reaction mixture was then diluted with dichloromethane (200 mL), and the organic fraction was extracted with water (5×100 mL), saturated sodium bicarbonate (3×50 mL), water (2×50 mL) and then saturated sodium chloride solution. The organic portion was dried over magnesium sulfate, filtered, and concentrated in vacuo to give crude 2-D-acetamido-3-octadecylthio-glycerol-benzoate (4.45 g). The crude (D)-2-acetamido-3-octadecylthio-glycerolbenzoate was diluted with tetrahydrofuran (10 mL) and exposed to 1N lithium hydroxide (10 mL) at about 23° for about 18 hours. The reaction mixture was then concentrated to remove the tetrahydrofuran and the aqueous solution extracted with dichloromethane (5×50 mL). The combined organics were washed with saturated sodium chloride solution, dried (magnesium sulfate), filtered and concentrated in vacuo. Pure (D)-2-acetamido-3-octadecylthio-glycerol (8B) was obtained by silica gel chromatography ($R_f$=0.36, 5% methanol in chloroform) and provided 264 mg, (61% yield).

8B: $[\alpha]^{25}$=+15.2°±2.0° (C=1.00, ethanol); NMR (360 MHz, CDCl$_3$): 6.08 (bd, J=6.0 Hz, 1H, NH), 4.05 (m, 1H, NCH), 3.80 (dd, J=4.0, 12.0 Hz, 1H, CH2O), 3.80 (dd, J=4.0, 12.0 Hz, 1H, CH2O), 3.70 (bd, J=12.0 Hz, 1H, CH2O), 2.72 (m, 2H, CH2S), 2.54 (t, J=8,0 Hz, 2H, CH2S), 1.75–1.20 (m, 32H), 0.88 (t, J=7.0 Hz, 3H, CH$_3$); IR (neat): 3440 (bw, NH), 3280 (bs, OH), 2910 (s), 2850 (s), 1735 (s, CON), 1380 (s), 1215 (s), 710 (s).

8A: (50% yield); NMR (90 MHz, CDCl$_3$), 6.10 (bs, 1H, NH), 5.40 (m, 2H, CH=CH), 4.05 (m, 2H, CHN), 3.80 (m, 2H, CH2O), 2.75 (d, J=6 Hz, 2H, CH2S), 2.70 (m, 2H, CH2C=), 2.60 (t, J=7.5, 2H, CH2S), 2.00 (s, 3H), CH$_3$); IR (CDCl3): 3400 (bs, OH, NH), 2910 (s), 2920 (s), 1670 (s, CON), 1600 (m), 1500 (m), 1480 ( ), 1420 (s), 1200 (s).

8C: (82% yield); NMR (90 MHz, CDCl$_3$), 6.15 (m, 1H, NH), 4.00 (m, 1H, CHN), 3.75 (m, 2H, CH2O), 2.70

(d, J=7.0 Hz, 2H, CH$_2$S), 2.50 (t, J=7.0 Hz, 2H, CH$_2$S), 2.00 (s, 3H, CH$_3$), 1.80–1.00 (m, 28H), 0.90 (t, J=7.0 Hz, 3H, CH$_3$); IR (CHCl$_3$), 3500 (bs), 3000 (s), 2970 (s), 2930 (s), 1675 (s, CON), 1600 (m, ), 1510 (m), 1425 (m), 1200 (s), 1040 (s).

8D: (93% yield); NMR (90 MHz, CDCl$_3$): 6.20 (bd, 7.0 Hz, 1H, NH), 4.00 (m, 1H, CHN), 3.80 (m, 2H, CH$_2$O), 3.30 (bm, 1H, OH), 2.70 (d, 6.0 Hz, 2H, CH$_2$S), 2.55 (t, J=7.0 Hz, 2H, CH$_2$S), 2.00 (s, 3H, CH$_3$CO), 1.80–1.10 (m, 12H), 0.95(t, J=7.0 Hz, 3H, CH$_3$); IR (CHCl$_3$): 3400 (bs, OH, NH), 3000 (s), 2920 (s), 2850 (s), 1665 (s, CON), 1500 (s), 1460 (m), 1380 (m), 1270 (w), 1045 (s).

8E: (64% yield); NMR (90 MHz, CDCl$_3$): 6.10 (bd, J=7.0 Hz, 1H, NH), 4.00 (m, 1H, CHN), 3.85 (m, 2H, CH$_2$O), 3.50 (bm, 1H, OH), 2.70 (d, J=7.0 Hz, 2H, CH$_2$S), 2.55 (t, J=7.0 Hz, 2H, CH$_2$S), 2.00 (s, 3H, CH$_3$CO), 1.80–1.10 (m, 8H), 0.95 (t, J=7.0 Hz, 3H, CH$_3$); IR (CHCl$_3$): 3400 (s), 3000 (s), 2950 (s), 2920 (s), 2850 (s), 1665 (s, CON), 1500 (s), 1460 (m), 1380 (m), 1040 (m).

G. Preparation of 3-Octadecylthio-2-acetamidophosphatidylcholine (10B)

Anhydrous triethylamine (distilled from calcium hydride) (0.4 mL) was added to a dry (distilled from benzophenone/sodium) tetrahydrofuran (20 mL) solution containing 3-octadecylthio-2-acetamido-gyclerol (8B) (1.5 g) at 0° under nitrogen. The resulting mixture was maintained at 0° and 2-chloro-2-oxo-1,2,3-dioxaphospholane (0.41 g) in dry tetrahydrofuran (5 mL) was added. The reaction mixture was then stirred and permitted to warm to about 23° during the next 24 hours. Thin layer chromatography showed that starting material 8B had been completely converted into the desired cyclic phosphate [R$_4$ (9)=0.25, R$_f$ (8B)=0.10; 10% methanol in chloroform]. The crude cyclic phosphate 9 was isolated by diluting the reaction mixture with tetrahydrofuran (20 mL), which was then filtered through a bed of magnesium sulfate and the resulting solution was concentrated in vacuo. The residue was dissolved in dry (distilled from calcium hydride) acetonitrile (10 mL) and transferred to a dry Carius tube. The reaction mixture was cooled to −78° with liquid nitrogen. While frozen, anhydrous (distilled through potassium hydroxide) trimethylamine (1 mL) was added, and the contents were sealed under vacuum. The reaction mixture was next permitted to warm to about 23°, and then the selaed tube was heated to 65° and kept at that temperature for 48 hours. The sealed tube was cooled and opened and the contents were evaporated in vacuo. The residue of the tube was subjected to medium pressure liquid chromatography (R$_f$ (10B)=0.15; chloroform, methanol, water; 65:25:4) and afforded 3-octadecyl-2-acetamido phosphatidylcholine (10B) (0.54 g, 33% yield).

10B: m.p. 198°–202°, [α]$^{25}$=+6.8°±0.8°, (C=1.03, methanol); NMR (360 MHz, 10% CD$_3$OD/CDCl$_3$): 4.25 (m, 2H, CH$_2$OP), 4.08 (m, 1H, NCH), 4.06 (m, 1H, CH$_2$OP), 3.98 (m, 1H, CH$_2$OP), 3.59 (m, 2H, CH$_2$N), 3.22 (s, 9H, N(CH$_3$)$_3$), 2.68 (d, J=7.0 Hz, 2H, CH$_2$S), 2.55 (t, J=7.0 Hz, 2H, CH$_2$S), 1.98 (s, 3H, CH$_3$CO), 1.57 (m, 2H, CH$_2$), 1.40–1.20 (m, 30H), 0.88 (t, J=7.0 Hz, 3H, CH$_3$); IR (KBr, cm$^{-1}$): 3400 (bs, NH, OH), 2920 (s, sat. CH), 2850 (s, sat. CH), 1655 (s, CON), 1550 (m, CONHR), 1245 (s, P=O), 1090 (s, POC); FAB-MS (glycerol): 1133 (10%, 2M.H+), 567 (22%, M.H+), 384 (8%, C$_{23}$H$_{46}$NOS+), 185 (100%, C$_5$H$_{15}$NO$_4$P.H+); EA for C$_{28}$H$_{57}$N$_2$O$_5$PS.2H$_2$O: calcd.: C 55.97%, H 10.23%, N 4.66%, S 5.34%, P 5.16%); found: C 56.82%, H 9.81%, N 4.94%, S 5.73%, P 5.25%.

10A: (38% yield); m.p.=190°–200°, [α]$^{25}$=+12.2°±0.8°, (C=1.10, methanol); NMR (360 MHz, 10% CD$_3$OD/CDCl$_3$), 5.35 (m, 2H, CH=CH), 4.38 (m, 2H, CH$_2$OP) 4.05 (m, 2H, NCH, CH$_2$OP) 3.95 (m, 1H, CH$_2$OP), 3.69 (m, 2H, CH$_2$N), 3.22 (s, 9H, N(CH$_3$)$_3$), 2.68 (d, J=7.0 Hz, 2H, CH$_2$S), 2.55 (t, J=7.0 Hz, 2H, CH$_2$S), 2.02 (m, 4H, CH$_2$C=), 1.97 (s, 3H, CH$_3$CO), 1.57 (m, 2H, CH$_2$), 1.40–1.20 (m, 22H), 0.88 (t, J=7.0 Hz, 2H, CH$_2$S); IR (neat, cm$^{-1}$): 3400 (BS, NH, OH), 2920 (s, sat. CH), 2850 (s, sat. CH), 1650 (s, CON), 1555 (s, CONHR), 1240 (s, P=O), 1090 (s, POC); HRMS: calculated for C$_{25}$H$_{43}$NOS, 381.3065; found 381.3052, M+—C$_5$H$_{24}$O$_4$NP; FAB-MS (glycerol): 565 (M+H)+; EA for C$_{28}$H$_{59}$O$_5$N$_2$PS.2H$_2$O: calcd.: C 55.79%, H 10.53%, N 4.65%, S 5.32%, P 5.14%; found: C 56.42%, H 10.30%, N 4.39%, S 5.82%, P 5.12%.

10C: (58% yield); m.p. 185°–190° dec.; [α]$^{25}$=+8.2°±0.8°, (C=1.05, methanol); NMR (360 MHz, 10% CD$_3$OD/CDCl$_3$): 4.25 (m, 2H, CH$_2$OP), 4.08 (m, 1H, NCH), 4.06 (m, 1H, CH$_2$OP), 3.98 (m, 1H, CH$_2$OP), 3.59 (m, 2H, CH$_2$N), 3.22 (s, 9H, N(CH$_3$)$_3$), 2.70 (m, 2H, CH$_2$S), 2.56 (t, J=7.0 Hz, 2H, CH$_2$S), 2.00 (s, 3H, CH$_3$CO), 1.57 (m, 2H, CH$_2$), 1.40–1.20 (m, 28H), 0.88 (t, J=7.5 Hz, 3H, CH$_3$); IR (CHCl$_3$): 3300 (bs, NH, OH), 2920 (s, sat. CH), 2850 (m), 1665 (s, CON), 1560 (m), 1450 (m), 1240 (s), 1080 (s).

10D: (53% yield); m.p. 129°–130° dec.; [α]$^{25}$=12.7°±0.8°, (C=1.15; methanol); NMR (300 MHz, 10% CD$_3$OD/CDCl$_3$), 4.25 (m, 2H, CH$_2$O), 4.07 (m, 2H, CH$_2$O), 3.97 (m, 1H, CHN), 3.60 (m, 2H, CH$_2$N), 3.20 (s, 9H, (CH$_3$)$_3$N), 2.70 (d, J+7.0 Hz, 2H, CH$_2$S), 2.55 (t, J=7 Hz, 2H, CH$_2$S), 1.95 (s, 3H, CH$_3$CO), 1.58 (m, 2H, CH$_2$CH$_2$S), 1.40–1.20 (m, 10H(m 0.90 (t, J-7.0 Hz, 3H, CH$_3$); IR (CHCl$_3$):3220 (bs, OH, NH), 2920 (s, sat. CH), 2850 (m), 1655 (s, CON), 1550 (m), 1465 (m) 1220 (s), 1080 (s), 970 (m); EA for C$_{18}$H$_{39}$N$_2$O$_5$PS.2H$_2$O: calcd.: C 46.74%, H 9.37%, N 6.06%, S 6.93%, P 6.70%; found: C 44.66%, H 9.63%, N 6.29%, S 7.69%, P 6.41%.

10E: (50% yield); m.p. 60°–61° dec.; [α]$^{25}$=+11.1°±0.8°, (C=1.14, methanol); NMR (360 MHz, 10% CD$_3$OD/CDCl$_3$): 7.80 (bd, J=6.0 Hz, 1H, NH), 4.20 (m, 2H, CH$_2$OP), 4.00 (m, 3H, CH$_2$OP, CHN), 3.55 (m, 2H, CH$_2$N), 3.10 (s, 9H, N(CH$_3$)$_3$), 2.80 (d, J=6.0 Hz, 2H, CH$_2$S), 2.45 (t, J=7.0 Hz, 2H, CH$_2$S), 1.95 (s, 3H, CH$_3$CO), 1.50 (m, 2H, CH$_2$CH$_2$S), 1.35–1.10 (m, 6H), 0.80 (t, J=7.0 Hz, 3H, CH$_3$); IR (CHCl$_3$): 3240 (bs, NH, OH), 3950 (s, sat. CH), 3920 (s, sat. CH), 2850 (m), 1650 (s, CON), 1550 (m), 1460 (m), 1420 (w), 1370 (m), 1220 (s), 1080 (s), 1050 (m), 960 (s); FAB-MS, EA for C$_{16}$H$_{35}$N$_2$O$_5$PS.2H$_2$O: calcd.: C 44.23%, H 9.05%, N 6.45%, S 7.38%, P 7.13%; found: C 46.18%, H 9.18%, N 7.24%, S 8.23%, P 7.55%.

H. Preparation of (D)-2-amino-3-(octadecyl)-glycerol (11B)

To a dioxane (5 mL) solution of (D)-2-phenyl-3-(octadecyl-thiomethyl)-4,5-dihydro-oxazole (7B) (5.3 g) was added 6N sulfuric acid (10 mL). After refluxing for 48 hours, the reaction mixture was cooled and combined with saturated sodium chloride solution (50 mL). The aqueous fraction was extracted with diethyl ether (5×100 mL) and the combined organic fractions were dried over magnesium sulfate, filtered and concentrated in vacuo, ($R_4$ (11)=0.25, 10% methanol in chloroform) to provide pure 11B (3.56 g, 83% yield).

11B: (83% yield); NMR (360 MHz, CDCl$_3$): 3.65 (dd, J=10.0, 4.0 Hz, 1H, CH$_2$O), 3.41 (dd, J=10.0, 7.0 Hz, 1H, CH$_2$O), 3.00 (m, 1H, NCH), 2.65 (dd, J=4.3, 13.5 Hz, 1H, CH$_2$S), 2.52 (t, J=7.0 Hz, 2H, CH$_2$S), 2.45 (dd, J=13.5, 8.0 Hz, 1H, CH$_2$S), 1.80 (bs, 2H, NH$_2$), 1.58 (m, 2H, CH$_2$), 1.40-1.20 (m, 30H), 0.88 (t, J=7.0 Hz, 3H, CH$_3$); IR (CHCl$_3$): 3420, (bs, OH, NH), 3000 (s), 2920 (s), 2850 (s), 1460 (s), 1380 (w), 1080 (s).

11C: (35% yield); NMR (300 MHz, CDCl$_3$): 3.60 (m, 2H, CH$_2$O), 3.00 (m, 1H, CHN), 2.60 (m, 2H, CH$_2$S), 2.40 (m, 2H, CH$_2$S), 1.40-1.00 (m, 28H), 0.85 (t, J=7.0 Hz, 3H, CH$_3$); IR (CHCl$_3$): 3600 bm, NH), 3420 (bs, OH, 3000 (s), 2920 (s), 2850 (s), 1460 (s), 1375 (w), 1210 (s), 1090 (s).

I. Preparation of 3-hexadecylthio-2-carboxymethylamideglycerol (12CII)

Methylchloroformate (0.63 mL) was added to a dry (distilled over calcium hydride) dichloromethane (25 mL) solution of 3-hexadecylthio-2-amino-glycerol hydrochloride (11) (2.0 g) at 0° under a nitrogen atmosphere. Anhydrous triethylamine (1.9 mL) was added slowly to the resulting slurry at 0°. After 1 hour, the reaction mixture was allowed to warm to room temperature. The reaction was complete in 1 hour; at that time it was diluted with dichloromethane (200 mL) and quenched with water (50 mL). The combined organic fractions were extracted 4 times with dichloromethane (100 mL), then washed with a saturated sodium chloride solution, dried over magnesium sulfate, filtered, and concentrated in vacuo. The residue was subjected to silica gel chromatography ($R_f$ (12CII)=0.35, 5% acetone in dichloromethane) and provided pure 12CII (1.6 g, 79% yield).

12CII: NMR (90 MHz, CDCl$_3$): 5.20 (bm, 1H, NH), 3.90 (m, 1H, CHN), 3.75 (m, 2H, CH$_2$O), 3.65 (bm, 1H, OH), 2.70 (d, J=7.0 Hz, 2H, CH$_2$S), 2.50 (t, J=7.0 Hz, 2H, CH$_2$S), 1.80-1.10 (m, 28H), 0.85 (t, J=7.0 Hz, 3H, CH$_3$); IR (CHCl$_3$): 3580 (bm, NH), 3420 (bs, OH), 3000 (m), 2920 (s), 2850 (s), 1710 (s, CO$_2$N), 1510 (s), 1460 (m), 1340 (w), 1050 (s).

12BII: (53% yield); NMR (90 MHz, CDCl$_3$): 5.30 (bm, 1H, NH), 3.85 (m, 1H, CHN), 3.70 (m, 2H, CH$_2$O), 3.45 (m, 1H, OH), 2.75 (d, J=7.0 Hz, 2H, CH$_2$S), 2.50 (t, J=7.0 Hz, 2H, CH$_2$S), 1.70-1.10 (m, 32H), 0.80 (t, J=7.0 Hz, 3H, CH$_3$); IR (CHCl$_3$): 3600 (bs, NH), 3430 (bs, OH), 3000 (s), 2920 (s), 2850 (s), 1700 (s), 1505 (s), 1460 (s), 1350 (m), 1050 (s).

J. Preparation of (D)-2-octadecyl-3-octadecylglycerol (12BI)

Stearic anhydride (10 g) was added to a solution (5 mL) of 7B (1.0 g) in tetrahydrofuran at about 23° under nitrogen. The components were completely mixed, then para-toluenesulfonic acid monohydrate (0.5 g) was added and the resulting reaction mixture was heated 3 hours at 120°. The solvent was removed by evaporation, leaving a brown solid which was diluted with ether (200 mL) and extracted 3 times with saturated sodium bicarbonate solution (50 mL). The organic phase was then shaken successively with water (50 mL), and saturated sodium chloride solution (50 mL), and then dried over magnesium sulfate, filtered and concentrated in vacuo. The residue was purified by silica gel chromatography ($R_f$=0.75, 25% ethyl acetate in hexane) to provide the required amide benzoate contaminated with excess stearic anhydride. The mixture was diluted with tetrahydrofuran (50 mL) and combined with excess 1N lithium hydroxide (50 mL) solution and permitted to stir 24 hours at about 23°. The tetrahydrofuran was removed by evaporation (in vacuo). The resulting aqueous phase was shaken with ether (3×100 mL) and the combined organic layers were repeatedly extracted with 2N sodium hydroxide solution (4×50 mL). The resulting organic phase was washed with water (50 mL), saturated sodium chloride (50 mL), then dried over magnesium sulfate, filtered and concentrated in vacuo. Purification of the residue by silica gel chromatography ($R_f$(12BI)=0.45, 5% methanol in chloroform) supplied pure 12BI (0.23 g) in 17% yield.

12BI: NMR (360 MHz, CDCl$_3$): 4.00 (m, 1H, NCH), 3.72 (dd, J=12.0, 5.0 Hz, 1H, CH$_2$O), 3.62 (dd, J=12.0, 5.0 Hz, 1H, CH$_2$O), 2.70 (t, J=8.0 Hz, 2H, CH$_2$S), 2.54 (t, J=8.0 Hz, 2H, CH$_2$S), 2.20 (5, J=8.0 Hz, 2H, CH$_2$CO), 1.65-1.20 (m, 62H), 0.88 (t, J=7.2 Hz, 6H, CH$_3$); IR (CHCl$_3$): 3430 (bs, OH, NH), 2930 (s), 2850 (s), 1660 (s, CON), 1510 (s), 1465 (s), 1360 (m), 1300 (m).

K. Preparation of 2-phenacylamino-3-hexadecathiomethylglycerol (12CIV)

Aqueous 1N hydrochloric acid (25 mL) was added to 7C (1 g) and the resulting mixture was refluxed for 3 hours. The mixture was then cooled and neutralized (pH=7.0) by adding saturated sodium carbonate solution. It was then extracted with dichloromethane (3×100 mL). The combined organic fractions were washed with water (100 mL) and saturated sodium chloride and then dried over magnesium sulfate, filtered and concentrated in vacuo. The residue was dissolved in tetrahydrofuran (5 mL) and methanol (5 mL) and the resulting solution was combined with 1N lithium hydroxide solution (5 mL) at about 23°. The reaction mixture was incubated for 1 hour, quenched with saturated ammonium chloride solution (25 mL), and then extracted with diethyl ether (3×100 mL). The combined organic fractions were dried over magnesium sulfate, filtered and concentrated in vacuo. The residue was subjected to silica gel chromatography ($R_f$ (12CIV)=0.35, 5% acetone in dichloromethane) to afford purified amide alcohol 12CIV (0.9 g, 85% yield).

12CIV: NMR (300 MHz, CDCl$_3$): 7.80 (m, 2H, phenyl), 7.50 (m, 3H, phenyl), 6.80 (m, 1H, NH), 4.30 (m, 1H, CHN), 3.80 (m, 2H, CH$_2$O), 2.90 (m, 2H, CH$_2$S), 2.60 (t, J=7.0 Hz, 2H, CH$_2$S), 2.40 (bm, 1H, OH), 1.80-1.10 (m, 28H), 0.90 (t, J=7.0 Hz, 3H, CH$_3$); IR (CHCl$_3$): 3420 (bm, NH, OH), 3000 (w), 2920 (s), 2850 (s), 1665 (s), 1580 (m), 1520 (s), 1480 (s), 1460 (m), 1080 (m), 880 (w).

L. Synthesis of Phospholipids of the 13 Series

Phospholipids 13 were prepared from corresponding glycerols 12 by procedures substantially similar to those described for conversion of 3-octadecylthio-2-acetamido-glycerol (8B) to 3-octadecylthio-2-acetamidophosphatidylcholine (10B) in part I, above 13CIV: (20% yield), m.p.=170°-175° dec.; $[\alpha]^{25}$=21.5°±0.8°, (C=1.27, methanol); NMR (300 MHz, 10% CD$_3$OD/CDCl$_3$): 8.40 (bd, J=5 Hz, NH), 7.80 (m, 2H, phenyl), 7.35 (m, 3H, phenyl), 4.30 (m, 2H, CH$_2$OP), 4.20 (m, 2H, CH$_2$OP, CHN), 4.05 (m, 1H, CH$_2$OP), 3.45 (m, 2H, CH$_2$N), 3.15 (s, 9H, N(CH$_3$)$_3$), 2.75 (d, J=7.5 Hz, 2H, CH$_2$S), 2.50 (t, J=7.0 Hz, 2H, CH$_2$S), 1.60 (m, 2H, CH$_2$CH$_2$S), 1.40–1.20 (m, 28H), 0.90 (t, J=7.0 Hz, 3H, CH$_3$); IR (CHCl$_3$): 3300 (bs, OH, NH), 3000 (m), 2920 (s), 2850 (s), 1660 (s, CON), 1570 (m), 1450 (m), 1420 (m), 1080 (s), 970 (s), EA for C$_{31}$H$_{57}$N$_2$O$_5$PS.2H$_2$O: calcd: C 58.46%, H 9.65%, N 4.40%, S 5.03%, P 4.86%; found: C 59.55%, H 9.34%, N 4.36%, S 5.81%, P 5.15%.

13BII: (63% yield); m.p. 215°–220° dec; $[\alpha]^{25}$ = +7.1°±0.80°, (C=1.07 g, methanol); NMR (360 MHz, 10% CD$_3$OD/CDCl$_3$): 4.27 (m, 2H, CH$_2$OP), 4.05 (m, 1H, CH$_2$OP), 3.98 (m, 1H, CH$_2$O), 3.85 (m, 1H, NCH), 3.65 (s, 3H, OCH$_3$), 3.63 (m, 2H, CH$_2$N), 3.23 (s, 9H, N(CH$_3$)$_3$), 2.70 (d, J=7.0 Hz, 2H, CH$_2$S), 2.55 (t, J=7.5 Hz, 2H, CH$_2$S), 1.57 (m, 2H, CH$_2$), 1.40–1.20 (m, 30H), 0.88 (t, J=7.0 Hz, 3H, CH$_3$); IR (CHCl$_3$): 3250 (bs, NH, OH), 2920 (s), 2850 (m), 1705 (s, CO$_2$N), 1460 (s), 1390 (w), 1085 (s), 970 (m); EA for C$_{28}$H$_{59}$N$_2$O$_6$PS.2H$_2$O: calcd: C 54.34%, H 10.26%, N 4.53%, S 5.18%, P 5.01%; found: C 53.82%, H 10.20%, N 4.31%, S 5.70%, P 5.12%.

13CII: (63% yield ); m.p.=220°–223° dec.; $[\alpha]^{25}$=+6.8°±0.8°, (C=1.03, methanol), NMR (360 MHz, 10% CD$_3$OD, CDCl$_3$): 4.25 (m, 2H, CH$_2$OP), 4.05 (m, 1H, CH$_2$OD), 3.98 (m, 1H, CH$_2$OP), 3.84 (m, 1H, NCH), 3.65 (s, 3H, OCH$_3$), 3.62 (m, 2H, CH$_2$N), 3.32 (s, 9H, N(CH$_3$)$_3$), 2.70 (d, J=6.0 Hz, 2H, CH$_2$S), 2.55 (t, J=7.0 Hz, 2H, CH$_2$S), 1.57 (m, 2H, CH$_2$), 1.40–1.20 (m, 26H), 0.88 (t, J=7.0 Hz, 3H, CH$_3$); IR (CHCl$_3$): 3300 (bs, NH, OH), 2930 (s), 2860 (m), 1750 (s, CO$_2$N), 1450 (s), 1390 (w), 1090 (s), 970 (m).

13BI: (17% yield); m.p.=165°–170°; $[\alpha]^{25}$=+7.5°±0.2°, (1.20, methanol:chloroform, 1:4); NMR (300 MHz, CDCl$_3$): 7.80 (m, 1H, NH), 4.20 (m, 2H, CH$_2$OP), 4.00 (m, 2H, CH$_2$OP, CHN), 3.90 (m, 1H, CH$_2$OP), 3.50 (m, 2H, CH$_2$N), 3.10 (s, 9H, N(CH$_3$)$_3$), 2.80 (d, J=7.0 Hz, 2H, CH$_2$S), 2.50 (t, J=7.0 Hz, 2H, CH$_2$S), 2.10 (t, J=7.0 Hz, 2H, CH$_2$CO), 1.50 (m, 2H, CH$_2$CH$_2$S), 1.50–1.10 (m, 63H), 0.80 (t, J=7.0 Hz, 3H, CH$_3$); IR (CHCl$_3$): 3250 (bw, NH, OH), 2920 (s), 2850 (s), 1660 (m, CON), 1550 (w), 1460 (m), 1370 (w), 1080 (s), 970 (m), EA for C$_{44}$H$_{91}$N$_2$O$_5$PS.2H$_2$O: calcd: C 63.88%, H 11.58%, N 3.93%, S 3.88%, P 3.74%; found: C 63.24%, H 11.67%, N 3.20%, S 4.51%, P 3.93%.

Utility

The product compounds of the present invention (Formula I) selectively induce significant reductions in the blood pressure of experimental animals in which hypertension is a spontaneous and chronic condition. In addition, the compounds of the invention have been demonstrated to significantly inhibit the inflammatory response caused by a noxious agent when applied topically just prior to the noxious stimulant. This evidence clearly indicates the utility of the compounds of Formula I in various pharmaceutical formulations for use in human and/or veterinary applications.

The compounds of the invention can be administered intravenously, intramuscularly, intraperitoneally, or topically to a warm-blooded animal following dispersal or solution in a pharmaceutically suitable diluent or vehicle.

For the purpose of this invention, a warm-blooded animal means a member of the animal kingdom having a homeostatic mechanism; the term includes mammals and birds.

I. EXAMPLES 2–8

Antihypertensive Activity

The compounds of this invention can be administered in the treatment of hypertension by any means resulting in contact of the active ingredient compound with the site of action in the body of a warm-blooded animal. For example, administration can be parenteral, i.e., intravenous.

Appropriate and effective dosages of the compounds of Formula I to be administered in treating of hypotension will be determined by the age, health, and weight of the recipient; the extent of disease; nature of of concurrent treatment, is any; frequency of treatment; and the nature of the effect desired.

Usually, a daily dosage of active ingredient compound will be from about 0.1 to 100 milligrams per kilogram (mg/kg) of body weight. Ordinarily, from 0.2 to 60, and preferably 1.0 to 40 mg/kg per day in one or more applications is effective to obtain the desired results. For the more potent compounds of the invention, e.g. 10A, daily dosages range from about 0.1 to 20 mg/kg, preferably 0.2 to 20 mg/kg, and more preferably from 0.5 to 5 mg/kg.

EXAMPLE 2

The antihypertensive activity of 3-octadecylthio-2-carbomethoxyamidophosphatidylcholine (compound 13BII) was demonstrated by tests conducted using the spontaneous hypertensive rat (SHR). In this procedure, anesthetized rats were dosed intravenously with graded dose levels the test compound on a cumulative dose schedule. The test compound was administered in an aqueous 0.25% methylcellulose vehicle at a volume to body weight ratio of 1 mL/kg. Arterial blood pressure was continuously recorded directly through an arterial cannula and a polygraph. That dose of compound producing a reduction in mean blood pressure of 30 mm Hg, or ED$_{30}$, was then determined. In this manner, an ED$_{30}$ of 2.00 mg/kg was determined for compound 13BII.

EXAMPLES 3–8

The antihypertensive activity of other compounds within the scope of the present invention was determined by methods substantially similar to those reported in Example 2, above, except that intravenous dosage levels of 2 and 12 mg/kg were employed. The results of these tests are indicated in Table I, below. The designation "prolonged" indicates a hypotensive response lasting from 15–30 minutes. The following designations are employed to indicate the magnitude of hypotensive response:

TABLE I

Blood Pressure Responses to Analogs of Platelet Activating Factor in Spontaneous Hypertensive Rat

| Ex. | Compound | R$^1$ | R$^2$ | Dosage (mg/kg) | Response | Duration |
|---|---|---|---|---|---|---|
| 3 | 10A | 9Δ—C$_{18}$H$_{35}$ | CH$_3$ | 2 | ++ | prolonged |
| 4 | 10B | C$_{18}$H$_{37}$ | CH$_3$ | 2 | ++ | prolonged |
| 5 | 13CII | C$_{16}$H$_{33}$ | CH$_3$O | 2 | ++ | prolonged |
| 6A | 13BII | C$_{18}$H$_{37}$ | CH$_3$O | 2 | ± | — |
| 6B | 13BII | C$_{18}$H$_{37}$ | CH$_3$O | 12 | ++ | prolonged |
| 7A | 10D | C$_8$H$_{17}$ | CH$_3$ | 2 | NE | — |

TABLE I-continued

Blood Pressure Responses to Analogs of Platelet Activating Factor in Spontaneous Hypertensive Rat

| Ex. | Compound | $R^1$ | $R^2$ | Dosage (mg/kg) | Response | Duration |
|---|---|---|---|---|---|---|
| 7B | 10D | $C_8H_{17}$ | $CH_3$ | 12 | ++ | prolonged |
| 8A | 13CIV | $C_{16}H_{33}$ | Ph | 2 | NE | — |
| 8B | 13CIV | $C_{16}H_{33}$ | Ph | 12 | ± | — |

++: Pronounced decrease in blood pressure (>50 mm Hg)
+: Moderate decrease in blood pressure (35–50 mm Hg)
±: Threshold decrease in blood pressure (25–35 mm Hg)
NE: No effect observed

II EXAMPLES 9-10

Topical Anti-inflammatory Activity

Topical application of tetradecanoyl phorbol acetate (TPA) to murine skin results in an inflammatory reaction characterized by edema, a dense cellular infiltration 4–6 hours later, and an epidermal hyperplasia 24 hours following application. (Kuehl et al., Nature 265:170 (1977). One of the earliest events characteristic of the epidermal response to TPA is release of prostaglandin $E_2$ (PGE$_2$). PGE$_2$ is produced and released in response to activation of phospholipase $A_2$ and release of arachidonic acid. (Ashendel et al. *Biochem. Biophys. Res. Comm.* 90:623 (1979); Bresnick et al., *Cancer Letters* 7: 121–125, (1979); Furstenberger et al., *Biochem. Biophys. Res. Comm.* 92:749 (1980)). Various antiinflammatory agents inhibit this reaction; the most potent are the corticosteroids. (Viaje et al., *Cancer Research* 37:1530 (1977)). Cyclo-oxygenase inhibitors also inhibit this reaction (Viaje et al., *Cancer Research* 37:1530 (1977).

To evaluate the antiinflammatory activity of certain compounds within the scope of the present invention, TPA was applied topically to ear epidermal tissue of male CF1 mice 4–6 weeks old. One μg of TPA in acetone was applied topically to one ear, while acetone only was applied to the contralateral ear of each mouse. Test compounds to be evaluated as antiinflammatory agents were applied to both ears in acetone just prior to application of TPA. Four hours after the application of the TPA, the animals were sacrificed, and 6 mm disks of tissue were excised from each treated ear and weighed. The relative amount of edema was then assessed by determining the difference in mass between control and TPA-treated tissue samples. The results obtained are set forth in Table II, below:

TABLE II

Topical Antiinflammatory Activity of Analogs of Platelet Activating Factor

| Example | Compound | $R^1$ | $R^2$ | Ear Volume Reduction (%) |
|---|---|---|---|---|
| 9 | 13CIV | $C_{16}H_{33}$ | Ph | 57 |
| 10 | 10B | $C_{18}H_{37}$ | $CH_3$ | 10 |

III. EXAMPLES 11-19

Inhibition of Phospholipase $A_2$

Inhibition of porcine pancreatic PLA$_2$ was measured by a modification of the assay used by Hirata et al., *Proc. Natl. Acad. Sci. USA* 77:533 (1980). The enzyme-substrate reaction was run in a total volume of 0.1 mL with the enzyme at a final concentration of 19 units/mL (0.025 ug protein/mL) which gave approximately 4000–8000 dpm of activity in a buffer containing 25 mM Tris, 25 mM glycylglycine, 25 mM CaCl$_2$ and 0.75 mM EDTA (tetra sodium salt), pH 8.5. Compounds to be tested as inhibitors were added to an aliquot of enzyme and incubated for 2 minutes, and then the substrate, [arachidonyl-1-$^{14}$C] L-1-palmitoyl-2-arachidonyl phosphatidylcholine was added to provide a final concentration of 14.0 uM (80,000 dpm). The reaction was allowed to proceed for five minutes at 37°, and then halted by freezing the mixture in a dry ice-ethanol slurry. The arachidonic acid product was separated from unreacted substrate using silica gel columns.

All reactions were run in duplicate. Compounds to be tested were dissolved in 0.2M Tris-Cl, pH 8.5 or dissolved in DMSO and then diluted with Tris-Cl buffer (maximum DMSO concentration, 7%). An approximation of IC$_{50}$ (the concentration of compound which inhibits the phospholipase activity by 50 percent) was determined for each compound from a semilog plot of percent inhibition versus the final inhibitor concentration. The results of these determinations are set forth in Table III, below:

TABLE III

Inhibition of Phospholipase $A_2$ Activity by Analogs of Platelet Activating Factor

| Example | Compound | $R^1$ | $R^2$ | IC$_{50}$ (M) |
|---|---|---|---|---|
| 11 | 10A | 9Δ—$C_{18}H_{35}$ | $CH_3$ | $6.0 \times 10^{-7}$ |
| 12 | 10B | $C_{18}H_{37}$ | $CH_3$ | $5.2 \times 10^{-7}$ |
| 13 | 10C | $C_{16}H_{33}$ | $CH_3$ | $1.1 \times 10^{-6}$ |
| 14 | 10D | $C_8H_{17}$ | $CH_3$ | $9.0 \times 10^{-6}$ |
| 15 | 10E | $C_6H_{13}$ | $CH_3$ | $9.8 \times 10^{-5}$ |
| 16 | 13BI | $C_{18}H_{37}$ | $C_{17}H_{35}$ | $5.5 \times 10^{-7}$ |
| 17 | 13BII | $C_{18}H_{37}$ | $CH_3O$ | $1.9 \times 10^{-5}$ |
| 18 | 13CII | $C_{16}H_{33}$ | $CH_3O$ | $1.8 \times 10^{-5}$ |
| 19 | 13CIV | $C_{16}H_{33}$ | Ph | $1.4 \times 10^{-6}$ |

What is claimed is:

1. A compound of the formula

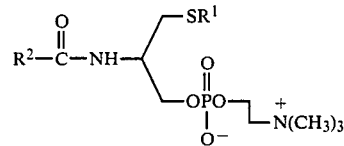

and physiologically acceptable salts thereof, wherein
 $R^1$ is $C_1$–$C_{25}$ alkyl, $C_1$–$C_{25}$ alkenyl, $C_6$–$C_{30}$ aryl, or $C_7$–$C_{30}$ aralkyl; and
 $R^2$ is hydrogen, $C_1$–$C_{25}$ alkyl, $C_6$–$C_{30}$ aryl, $C_7$–$C_{30}$ aralkyl or alkaryl, $C_1$–$C_{25}$ alkoxy, $C_1$–$C_{25}$ alkenyloxy, $C_6$–$C_{30}$ aryloxy, or $C_7$–$C_{30}$ aralkyloxy or alkaryloxy.

2. A compound according to claim 1, wherein
 $R^1$ is $C_1$–$C_{25}$ alkyl, $C_1$–$C_{25}$ alkenyl, or $C_6$–$C_{30}$ aryl; and
 $R^2$ is hydrogen, $C_1$–$C_{25}$ alkyl, $C_6$–$C_{30}$ aryl, $C_1$–$C_{25}$ alkoxy, $C_1$–$C_{25}$ alkenyloxy, or $C_6$–$C_{30}$ aryloxy.

3. A compound according to claim 2, wherein
 $R^1$ is $C_8$–$C_{20}$ alkyl or $C_8$–$C_{20}$ alkenyl; and
 $R^2$ is $C_1$–$C_{25}$ alkyl, $C_1$–$C_{25}$ alkoxy, or $C_6$–$C_{30}$ aryl.

4. A compound according to claim 3, wherein
 $R^1$ is $C_{14}$–$C_{18}$ alkyl or $C_{14}$–$C_{18}$ alkenyl; and
 $R^2$ is $C_1$–$C_{25}$ alkyl, $C_1$–$C_{25}$ alkoxy, or phenyl.

5. A compound according to claim 4, wherein
  $R^1$ is $C_{16}-C_{18}$ alkyl or $C_{16}-C_{18}$ *alkenyl; and*
  $R^2$ is methyl, methoxy, $C_{14}-C_{18}$ alkyl, or phenyl.

6. A compound according to claim 5,
wherein
  $R^1$ is a $9\Delta-C_{18}H_{35}$ alkenyl group; and
  $R^2$ is a methyl or phenyl.

7. A compound according to claim 6,
wherein
  $R^2$ is methyl.

8. A compound according to claim 6,
wherein
  $R^2$ is phenyl.

9. A compound according to claim 5,
wherein
  $R^1$ is a $C_{18}H_{37}$ alkyl group; and
  $R^2$ is a methyl, methoxy, or $C_{17}H_{35}$ alkyl group.

10. A compound according to claim 9,
wherein
  $R^2$ is methyl.

11. A compound according to claim 9,
wherein
  $R^2$ is methoxy.

12. A compound according to claim 5,
wherein
  $R^1$ is a $C_{16}H_{33}$ alkyl group; and
  $R^2$ is methyl, methoxy, $C_{14}-C_{18}$ alkyl, or phenyl.

13. A compound according to claim 12,
wherein
  $R^2$ is methoxy.

14. A therapeutic composition comprising an effective amount of a compound of claim 1 and a pharmaceutically acceptable vehicle or diluent.

15. A therapeutic composition comprising an effective amount of a compound of claim 2 and a pharmaceutically acceptable vehicle or diluent.

16. A therapeutic composition comprising an effective amount of a compound of claim 3 and a pharmaceutically acceptable vehicle or diluent.

17. A therapeutic composition comprising an effective amount of a compound of claim 4 and a pharmaceutically acceptable vehicle or diluent.

18. A therapeutic composition comprising an effective amount of a compound of claim 5 and a pharmaceutically acceptable vehicle or diluent.

19. A therapeutic composition comprising an effective amount of a compound of claim 6 and a pharmaceutically acceptable vehicle or diluent.

20. A therapeutic composition comprising an effective amount of a compound of claim 7 and a pharmaceutically acceptable vehicle or diluent.

21. A therapeutic composition comprising an effective amount of a compound of claim 8 and a pharmaceutically acceptable vehicle or diluent.

22. A therapeutic composition comprising an effective amount of a compound of claim 9 and a pharmaceutically acceptable vehicle or diluent.

23. A therapeutic composition comprising an effective amount of a compound of claim 10 and a pharmaceutically acceptable vehicle or diluent.

24. A therapeutic composition comprising an effective amount of a compound of claim 11 and a pharmaceutically acceptable vehicle or diluent.

25. A therapeutic composition comprising an effective amount of a compound of claim 12 and a pharmaceutically acceptable vehicle or diluent.

26. A therapeutic composition comprising an effective amount of a compound of claim 13 and a pharmaceutically acceptable wehicle or diluent.

* * * * *